United States Patent [19]
Gourlay et al.

[11] Patent Number: 5,304,183
[45] Date of Patent: Apr. 19, 1994

[54] TETHERED CLAMP RETRACTOR

[75] Inventors: Stuart J. Gourlay, Pinole; Terry Buelna, Rancho Santa Margarita; Wayne A. Noda, Mission Viejo; Paul Lubock, Laguna Niguel, all of Calif.

[73] Assignee: Laparomed Corporation, Irvine, Calif.

[21] Appl. No.: 855,766

[22] Filed: Mar. 23, 1992

[51] Int. Cl.⁵ .............................................. A61B 17/00
[52] U.S. Cl. .................................... 606/142; 606/41; 606/151; 606/158; 606/205; 606/210; 227/901; 227/902
[58] Field of Search ............... 606/142, 148, 151, 157, 606/158, 205-208; 227/901, 902

[56] References Cited

U.S. PATENT DOCUMENTS

| | | | |
|---|---|---|---|
| 1,274,669 | 8/1918 | Bohn . | |
| 2,549,731 | 4/1951 | Wattley . | |
| 3,404,677 | 10/1968 | Springer . | |
| 3,809,094 | 5/1974 | Cook . | |
| 3,877,434 | 4/1975 | Ferguson et al. | 606/148 |
| 4,051,844 | 10/1977 | Chiulli . | |
| 4,174,715 | 11/1979 | Hasson . | |
| 4,177,813 | 12/1979 | Miller et al. | 606/158 |
| 4,374,523 | 2/1983 | Yoon | 606/206 |
| 4,393,872 | 7/1983 | Reznik et al. . | |
| 4,519,392 | 5/1985 | Lingua | 606/157 |
| 4,605,990 | 8/1986 | Wilder et al. . | |
| 4,607,620 | 8/1986 | Storz . | |
| 4,681,107 | 7/1987 | Kees, Jr. | 606/142 |
| 4,706,668 | 11/1987 | Backer | 606/142 |
| 4,777,949 | 10/1988 | Perlin | 606/158 |
| 4,779,616 | 10/1988 | Johnson | 606/148 |
| 4,796,626 | 1/1989 | DeVries | 606/148 |
| 4,932,955 | 6/1990 | Merz et al. . | |
| 4,988,355 | 1/1991 | Leveen et al. . | |
| 4,990,157 | 2/1991 | Roberts et al. | 606/157 |
| 5,059,202 | 10/1991 | Liang et al. | 606/157 |
| 5,074,870 | 12/1991 | von Zeppelin . | |

FOREIGN PATENT DOCUMENTS 1452185 10/1976 United Kingdom .

Primary Examiner—Stephen C. Pellegrino
Assistant Examiner—Jeffrey A. Schmidt
Attorney, Agent, or Firm—Townsend and Townsend Khourie and Crew

[57] ABSTRACT

The invention provides a tissue manipulation system including a tethered clamp and a clamp applicator for positioning the clamp through a trocar sleeve and applying the clamp to a tissue location in the abdominal cavity. In a further embodiment, the tissue manipulation system includes a introducer through which the tether can be withdrawn from the abdominal cavity and a clamp attached to the proximal end of the introducer for clamping the tether in position. The tissue manipulation system further includes an obturator for inserting the introducer into the abdomen, and a tether snare for retrieving the tether and withdrawing it through the introducer.

39 Claims, 17 Drawing Sheets

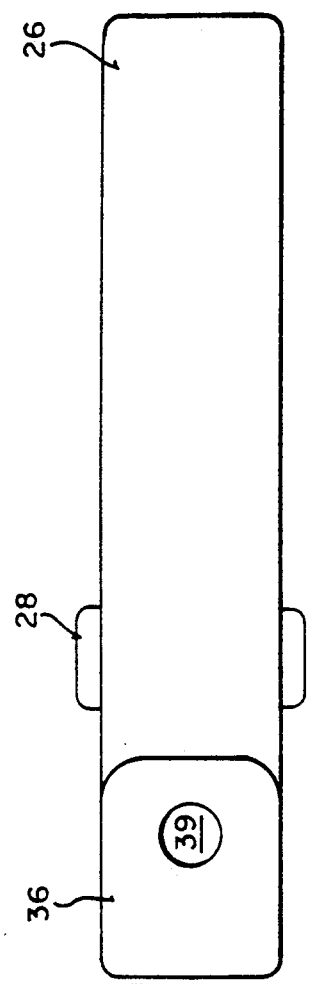
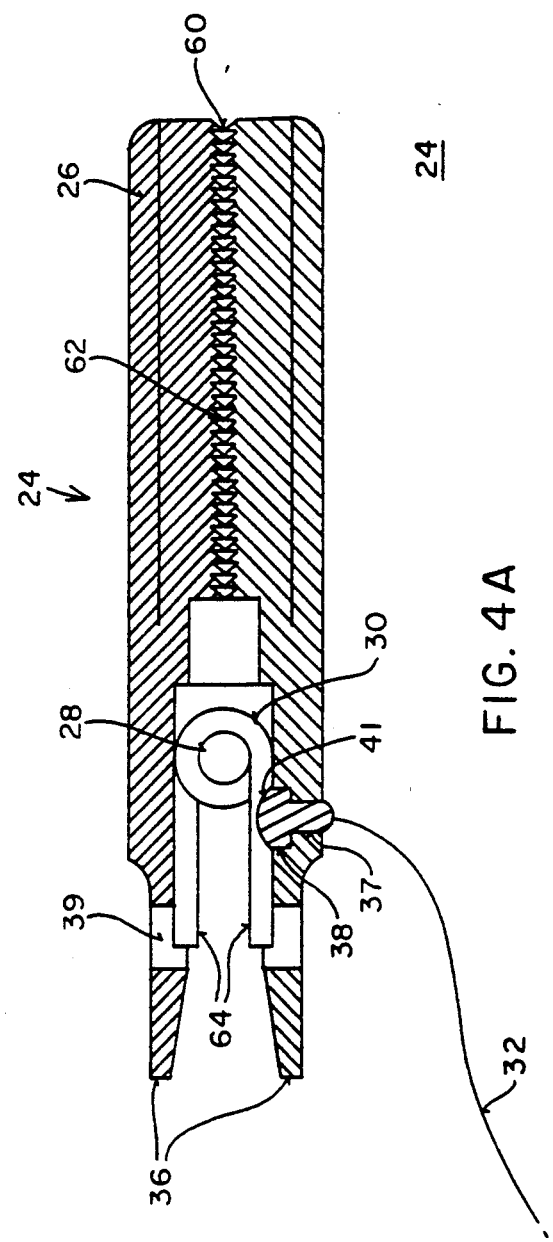
FIG. 4B
FIG. 4A

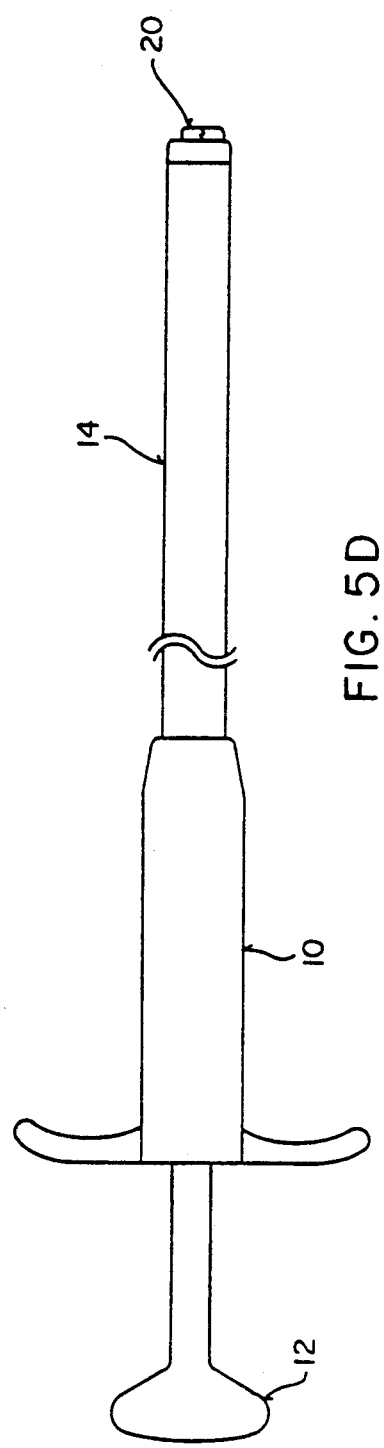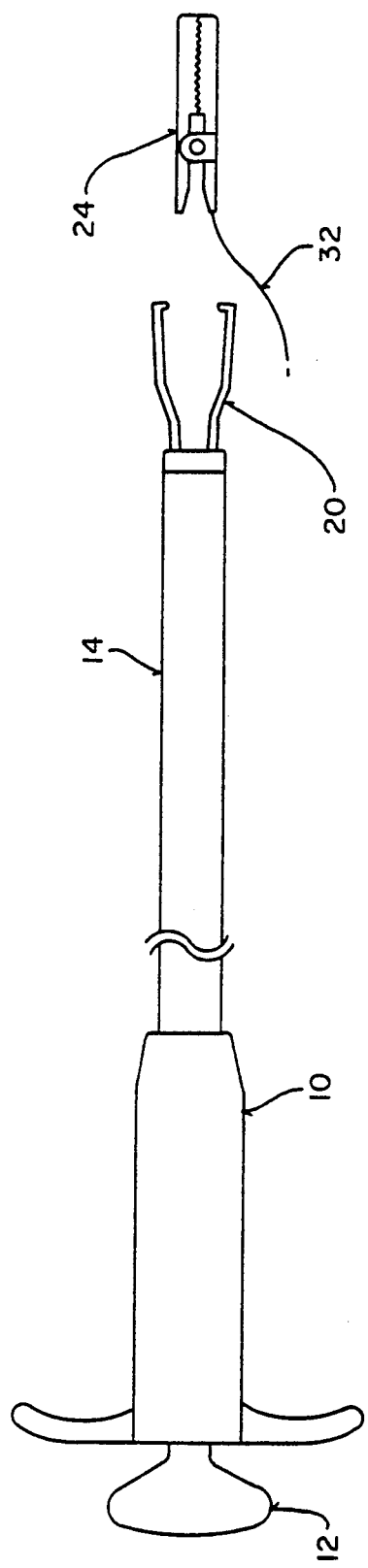

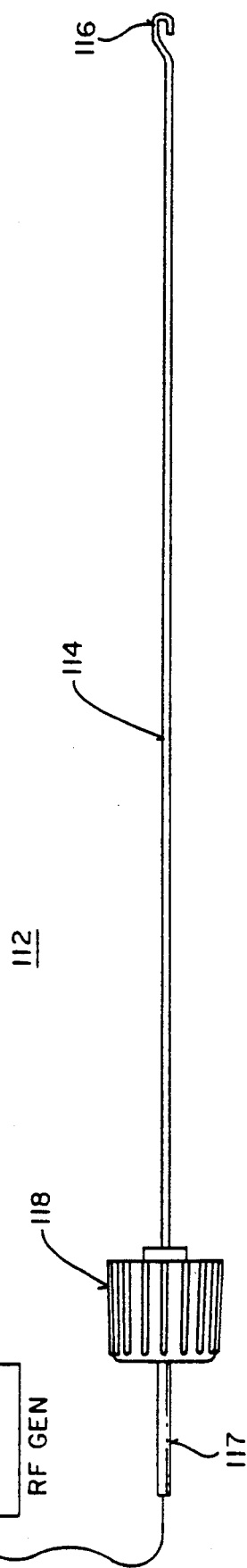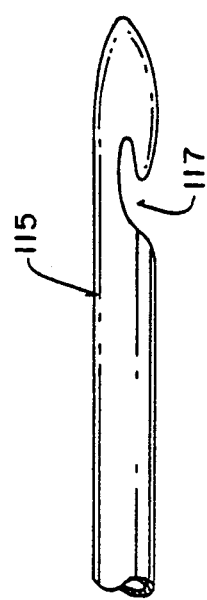
FIG. 9
FIG. 9A

TETHERED CLAMP RETRACTOR

BACKGROUND OF THE INVENTION

The present invention relates generally to surgical instruments, and more specifically to surgical instruments for tissue manipulation during surgical procedures, especially in laparoscopic surgery of the abdomen.

Laparoscopy facilitates the performance of a variety of surgical procedures of the abdomen, such as cholecystectomies, appendectomies, hernia repairs, hysterotomies and the like, without requiring large incisions or the invasive procedures of conventional surgical techniques. In laparoscopy, the abdominal cavity is distended using gas insufflation, so as to lift the wall of the abdominal cavity away from the underlying organs. A video scope is inserted through a cannula or trocar sleeve into the abdomen and connected to a monitor so as to provide visual guidance to the surgeon. One or more additional trocar sleeves are placed in the abdomen to allow introduction of surgical tools, such as retractors, cutting instruments and the like. Such trocar sleeves have a sealed passage through which instruments may be inserted, providing a leak-resistant entryway into the insufflated abdomen.

One disadvantage of laparoscopic surgical procedures is the limited access to the surgical site available to the surgeon. Entry to the site is limited to the small incisions or trocar sleeves through the abdominal wall. Any manipulation of internal tissue, for example, positioning a duct for ligation, or moving tissue to allow better access to or visibility of a particular location, must be performed using long handled instruments insertable through the trocar sleeves or incisions.

It is known to use surgical clamps or clamps for the purpose of clamping vessels or manipulating tissue. Typically, such clamps have a pair of movable jaws biased by a spring into a closed position, allowing the clamp to be placed on a vessel or portion of tissue and be firmly retained thereon. Examples of such clamps can be seen in U.S. Pat. No. 4,932,955 to Merz et al., U.S. Pat. No. 4,605,990 to Wilder et al., U.S. Pat. No. 5,074,870 to Von Zeppelin, U.S. Pat. No. 3,809,094 to Cook, U.S. Pat. No. 3,404,677 to Springer and U.S. Pat. No. 4,051,844 to Chiulli and U.S. Pat. No. 4,988,355 to Leveen et al.

It is also known in laparoscopic surgical procedures to use long-handled instruments for applying clamps to internal tissue within the abdominal cavity. Such clamp applicators typically include a pair of movable handles at the proximal end of the applicator and a pair of movable jaws at the distal end, wherein a clamp is placed in the jaws, the distal end of the applicator is inserted through a trocar sleeve into the abdomen and positioned at the desired tissue location, and the handles are actuated so as to apply the clamp to the tissue. Illustrative examples are seen in U.S. Pat. No. 4,174,715 to Hasson, and British Patent No. 1,452,185 to Wolf. Other tissue manipulation or clamping instruments with possible application to laparoscopic procedures are seen in U.S. Pat. No. 4,607,620 to Storz, U.S. Pat. No. 5,074,869 to Daicoff, U.S. Pat. No. 4,393,872 to Reznik et al., U.S. Pat. No. 2,549,731 to Wattley and U.S. Pat. No. 1,274,669 to Bohn.

However, known devices for manipulating tissue in laparoscopic procedures suffer from certain disadvantages. Known manipulating instruments typically have long, rigid members between the distal end and the handles at the proximal end, limiting the positionability of such devices. In addition, once such devices have been used to manipulate tissue to a desired position, the devices must be held in that position by the surgeon or an assistant. Further, the usefulness of known devices for positioning of tissue during laparoscopic procedures is limited by the necessity of having a trocar sleeve or incision in place proximate to the tissue to be manipulated in addition to those trocar sleeves being used for the surgical instruments employed in the procedure. Moreover, the size of known manipulation instruments requires that the additional trocar sleeve be of considerable size (e.g. 10 mm), increasing the invasiveness of the procedure.

For these and other reasons, an improved system and method for manipulating internal tissue during laparoscopic and other surgical procedures is desired. The system and method should allow greater flexibility in positioning from various points and at various angles. The system and method should allow positioning through a trocar sleeve or similar small access way and should minimize the need for placement of trocar sleeves in addition to those already in place for insertion of surgical instruments. Further, the system and method should allow the tissue to be maintained in a desired position without the need for ongoing manual intervention by the surgeon or an assistant.

SUMMARY OF THE INVENTION

The present invention provides a system and method for manipulating tissue and body structures in various surgical procedures, having particular usefulness in minimally-invasive procedures such as laparoscopic and endoscopic surgery. The invention allows internal tissue to be manipulated through a trocar sleeve or similar accessway and is highly flexible for positioning tissue from various angles. The system and method are simple and convenient, and do not require ongoing manual intervention once the tissue has been manipulated into a desired position. While being especially well-suited to minimally-invasive surgical techniques such as laparoscopy, endoscopy and arthroscopy, the tissue manipulation system and method of the invention are useful in any of a multitude of surgical procedures, including conventional open surgical procedures.

In one aspect of the invention, a tissue manipulation system comprises a clamp having a pair of movable jaws and means for closing and opening the jaws; means for applying the clamp to a first tissue site; and a flexible tether having a first end attached to the clamp and a free end opposite the first end for remotely manipulating the clamp. Usually, the means for applying the clamp comprises a clamp applicator having an elongated body with a distal end, a proximal end and an axial passageway therebetween; a pair of movable arms disposed at the distal end and configured to engage the means for closing and opening the jaws of the clamp; means at the proximal end of the body for actuating the arms; and a linkage disposed in an axial passageway, the linkage connecting the arms to the means for actuating. The clamp is preferably engaged by the clamp applicator such that the clamp may be rotationally positioned about at least 180° relative to the applicator.

In a further embodiment, the tissue manipulation system further includes means for retrieving the free end of the tether. Usually, the means for retrieving the tether comprises an elongated snare having a hooked end for grasping the tether.

Preferably, the tissue manipulation system further comprises means separated from the clamp for retaining the tether, so as to maintain the tissue in a desired position. In a preferred embodiment, the means for retaining the tether comprises an elongated cylindrical introducer having a distal end, a proximal end and an axial passageway therebetween, and a retainer disposed at the proximal end of the introducer, whereby the tether may be passed through an axial passageway and detachably secured in the retainer. Usually, the means for retrieving the tether is inserted through the introducer so as to draw the tether back through the introducer and into the retainer. By tensioning the tether, the tissue can be manipulated into position, and maintained in position by locking the tether in the retainer. In a preferred embodiment, the retainer comprises a stopcock attached to the proximal end of the introducer.

In a further aspect of the invention, a method for manipulating tissue comprises the steps of introducing a clamp having a flexible tether attached thereto through a percutaneous introducer to a tissue location; securing the clamp to the tissue location; and tensioning a free end of the tether to manipulate the tissue. Conveniently, the clamp may be introduced using a clamp applicator inserted through a trocar sleeve or cannula or equivalent.

Preferably, the step of tensioning the free end of the tether comprises pulling the free end through a percutaneous introducer. In addition, the method optionally includes the step of securing the tether relative to the introducer after tensioning the tether, usually by actuating a retainer disposed at the proximal end of the introducer. Alternatively, the method can include the step of retrieving the free end of the tether to facilitate removing the clamp from the tissue location.

In a further embodiment, the tether is secured by securing a second clamp, hook or other tissue engaging means attached to the tether internally to a second tissue location.

The introducer is percutaneously positioned, in one embodiment, by placing an obturator in the introducer and piercing through tissue at the desired location. In another embodiment, the introducer is positioned by applying radiofrequency (RF) energy to the tissue by means of an electrode situated at the distal end of the introducer. Preferably, the electrode comprises the hooked end of the tether snare, the hooked end being disposed at the distal end of a conductive rod, wherein the proximal end of the rod is coupled to an electrosurgical RF generator.

It should be understood that while the invention is described in the context of laparoscopic surgery of the abdomen, the tissue manipulation system and method disclosed herein are equally useful in other types of surgery, e.g. surgery of the pelvis or thorax, as well as in open surgical procedures.

A further understanding of nature and advantages of the invention may be realized by reference to the remaining portions of the specification and the drawings.

BRIEF DESCRIPTION OF THE DRAWING

FIGS. 4A and 4B are front and top elevational views of the clamp applicator of the present invention.

FIGS. 5A-5D are front elevational views of the clamp applicator of FIG. 1.

FIG. 9 is a front elevational view of a tether snare constructed in accordance with the principles of the present invention.

FIG. 9A is front view of a distal portion of a tether snare constructed in accordance with the principles of the present invention, illustrating an alternative configuration of the hooked end.

DETAILED DESCRIPTION OF THE ILLUSTRATIVE EMBODIMENTS

In a preferred aspect of the present invention, a tissue manipulation system includes a tethered clamp and a clamp applicator for positioning the clamp through a trocar sleeve in the abdominal cavity and applying the clamp to a tissue location. In a further embodiment, the tissue manipulation system comprises a introducer and a retainer attached to the proximal end of the introducer for retaining the tether. The invention further provides a tether snare insertable through the introducer for retrieving the tether and drawing it through the introducer to the retainer. In addition, the invention provides an obturator for percutaneously inserting the introducer.

Figures 1, 2:
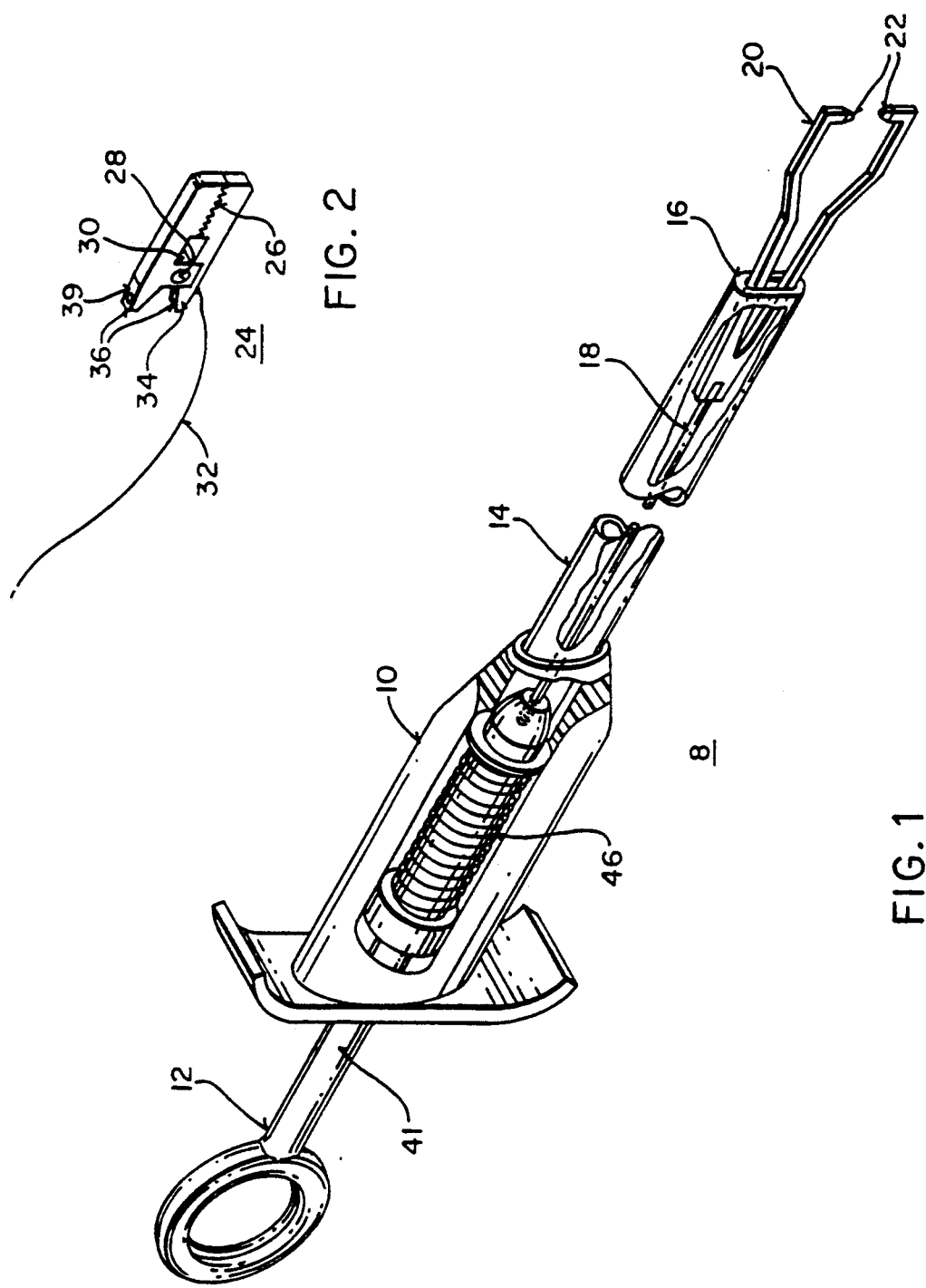
FIG. 1 is a perspective schematic of a clamp applicator constructed in accordance with the principles of the present invention.
FIG. 2 is a perspective view of a tethered clamp constructed in accordance with the principles of the present invention.

Referring to FIG. 1, the clamp applicator comprises a tubular handle 10, typically composed of polycarbonate or polysulfone, with a plunger 12 slidably mounted in the handle 10. Tubular extension 14, usually of polycarbonate or stainless steel, extends from the handle 10 distally and has a rectangular aperture 16 at its distal end.

Plunger 12 is coupled to a linkage 18 connecting plunger 12 to a pair of movable arms 20 disposed partially within extension 14 and partially extending from the distal end of extension 14. Arms 20 have a pair of tips 22 for engaging the tethered clamp.

As seen in FIG. 2, tethered clamp 24 has a pair of movable jaws 26 connected at hinge 28 and biased in a closed configuration by spring 30. Tether 32 is attached to a proximal portion 34 of levers 36. Levers 36 each have a depression 39 in which tips 22 of clamp applicator arms 20 engage.

Figure 3:
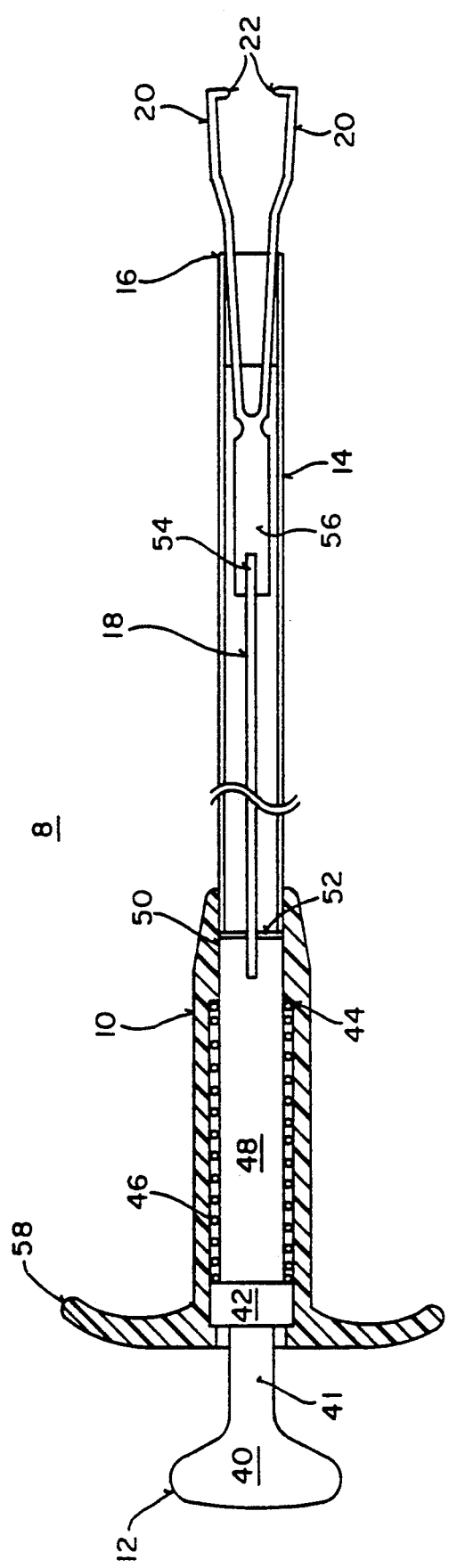
FIG. 3 is a front cross-sectional view of the clamp applicator of FIG. 1.

Referring now to FIG. 3, clamp applicator 8 will be described in greater detail. Plunger 12, usually of polycarbonate or polysulfone, has an actuator 40 typically comprising a ring (FIG. 1), knob (other FIGS.), or disc (not shown) at the proximal end of plunger 12 for moving the plunger in a distal or proximal direction. Actuator 40 is attached via shaft 41 to a retainer portion 42 which has a diameter corresponding to an aperture 44 within handle 10. A spring 46 is disposed around shaft 48 of plunger 12 and is retained within aperture 44 such that distal movement of plunger 12 exerts compressive force against spring 46 by retainer 42. Shaft 48 extends through bore 50 of handle 10 and terminates in a distal end 52. Linkage 18, usually a steel rod, is attached to distal end 52 of shaft 48 by threads, welding or other known means. Distal end 54 of linkage 18 is attached to a proximal portion 56 of arms 20. Arms 20, preferably of stainless steel, extend distally and angle laterally outward through aperture 16 such that arms 20 are resiliently biased in an open configuration. That is, when arms 20 are fully extended distally, tips 22 are furthest apart. Handle 10 further includes a pair of grips 58 configured to be grasped by the user's fingers when the plunger 40 is depressed by the thumb.

Figure 10A:
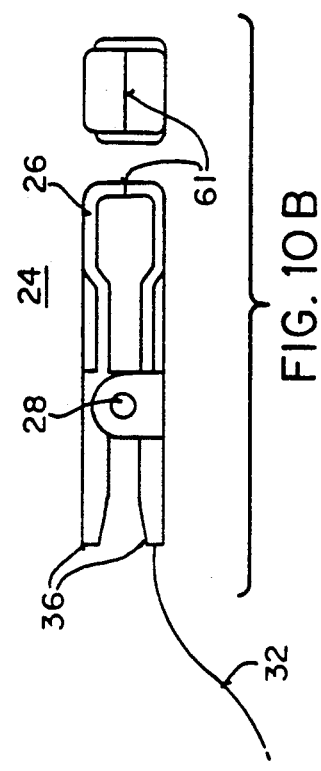
FIG. 10A is a front elevational view of the tethered clamp of FIG. 2.
Figure 10B:
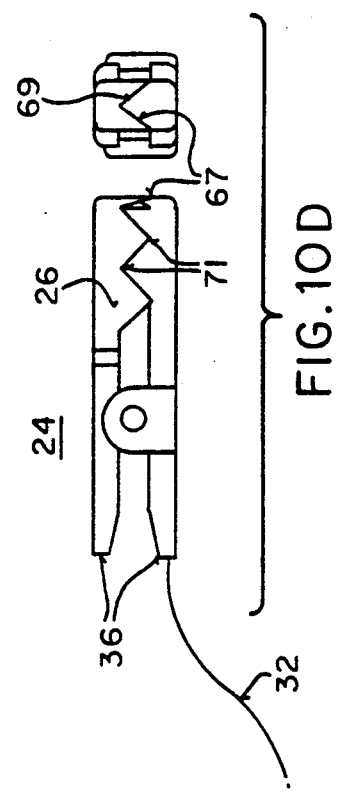
FIG. 10B is a front elevational view of an alternative embodiment of the clamp of FIG. 10A.
Figure 10C:
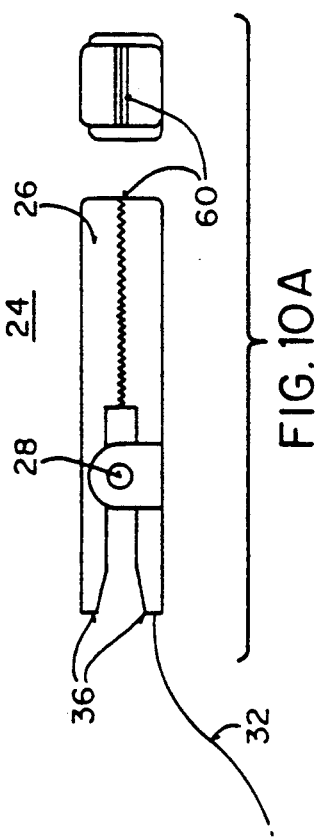
FIG. 10C is a front elevational view of an alternative embodiment of the clamp of FIG. 10A.
Figure 10D:
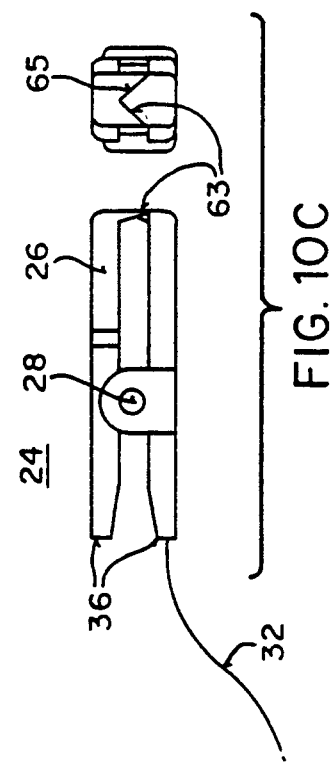
FIG. 10D is a front elevational view of an alternative embodiment of the clamp of FIG. 10A.

Referring now to FIGS. 4A and 4B, the tethered clamp 24 of the present invention will be described. Clamp 24 has a pair of movable jaws 26 contacting each other along contact plane 60 when jaws 26 are closed. In an "Atraumatic" embodiment, contact plane 60 has a plurality of teeth 62 for improved grip on tissue, as shown in FIG. 10A. In other embodiments, as shown in FIGS. 10B-10D, contact plane 60 of clamp 24 has various other configurations, depending upon the particular application. FIG. 10B illustrates a "Babcock" configuration, with jaws 26 meeting along a narrow, straight surface 61 at the distal end of the jaws. FIG. 10C illustrates the "Kocher" type, with jaws 26 meeting at an overlapping point 63 and notch 65 at the distal end of the jaws. In the "traumatic" type of FIG. 10D, jaws 26 meet in a point 67 and notch 69 at the distal end as in the "Kocher" type, and further contact each other along teeth 71 proximally of the distal end. Other clamp embodiments include, for example, Kelly, Allis, Glassman, Bulldog, DeBakey, and Cooley-type clamps, all of which may be used in conjunction with the present invention.

Jaws 26 are joined at hinge 28, which may comprise a pin or rivet. Spring 30 is disposed around hinge 28, with a pair of extensions 64 engaging levers 36. Spring 30 is configured to bias jaws 26 in a closed configuration by exerting outward force against levers 36. Tether 32 extends through bore 37 in one of levers 36 and is knotted within countersink 38, which is covered with adhesive 41. Tether 32 preferably comprises medical grade monofilament polyester, polyamide or polypropylene line load rated to 10 lbs. Alternatively, tether 32 may be elastic, so as to be resiliently extendable. Depressions 39 in levers 36 are shaped complementary to tips 22 of clamp applicator arms 20 to facilitate secure engagement. Levers 36 are engaged by tips 22 so as to permit clamp 24 to be rotationally positioned relative to clamp applicator 8 about an axis through tips 22.

In an alternative embodiment, the tether has a second clamp, hook, or other tissue engaging means detachably coupled to the tether between the first clamp and the free end of the tether. In this embodiment, the tether is tensioned to position the clamp 24, and the tissue engaging means coupled to the tether is attached to a second portion of tissue to maintain clamp 24 in position.

Figure 5A:
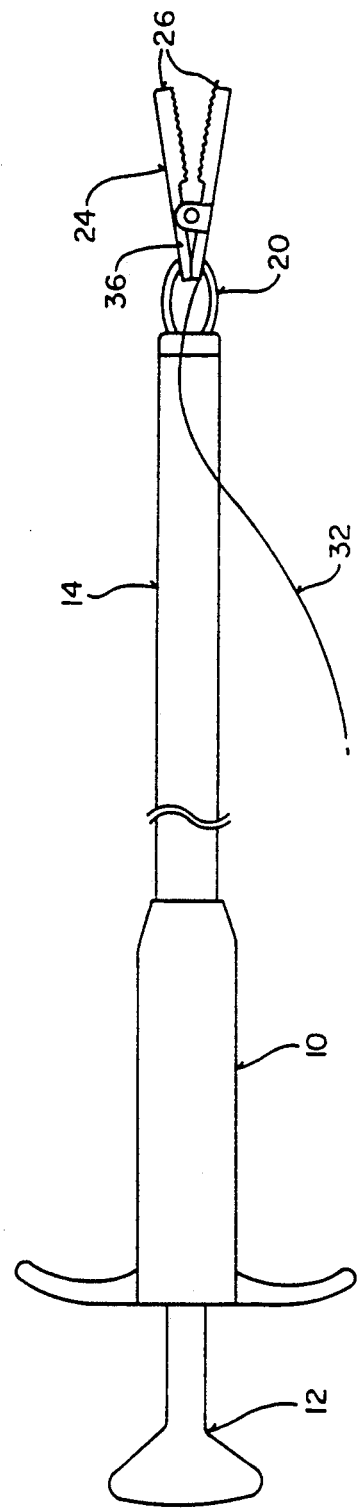
Figure 5B:
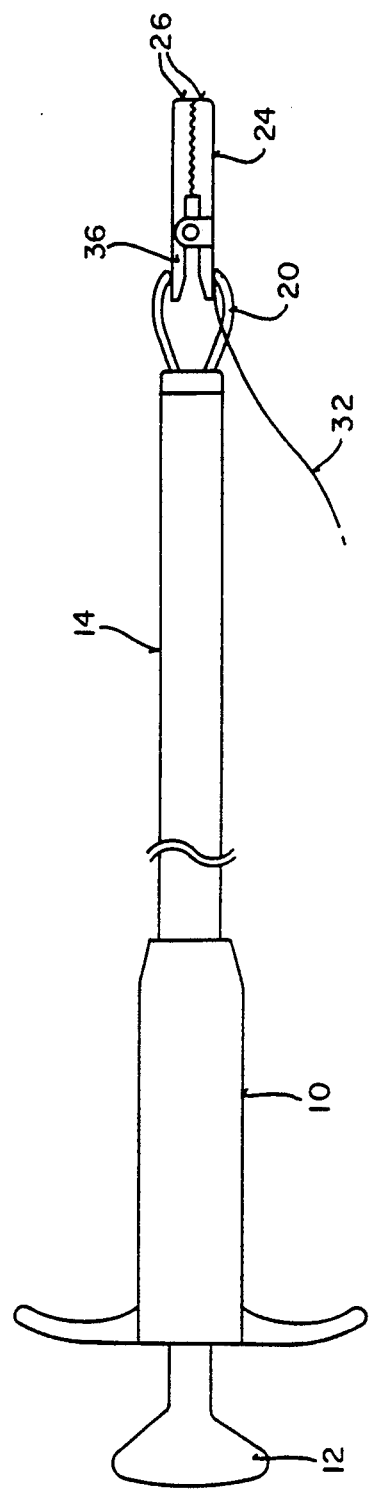

Referring to FIGS. 5A and 5B, it can be seen that when plunger 12 is extended proximally of handle 10, arms 20 are retracted into extension member 18 moving arms 20 toward each other and pressing levers 36 such that jaws 26 are opened. When plunger 12 is pushed in a distal direction, arms 20 move distally and away from each other, allowing levers 36 to move apart and closing jaws 26. As shown in FIG. 5C, pushing plunger 12 to its distal-most position extends arms 20 so that the gap between tips 22 is wider than the distance between levers 36, allowing the clamp applicator to be disengaged from clamp 24. As shown in FIG. 5D, pulling plunger 12 to its most proximal position fully retracts arms 20 into aperture 16 of extension 14.

Figure 6:
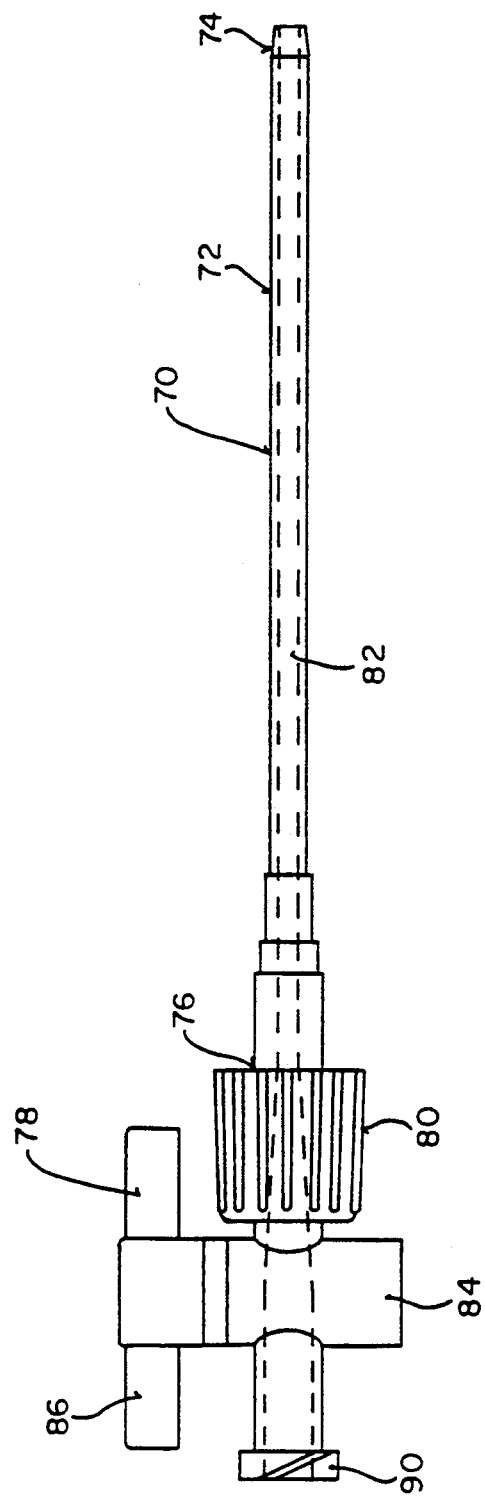
FIG. 6 is a introducer and stopcock constructed in accordance with the principles of the present invention.

Referring now to FIG. 6, the introducer/stopcock assembly will now be described. Introducer 70 comprises a tubular shaft 72, usually of medical grade polyurethane, PVC or polyethylene, having a taper 74 at its distal end and a female luer lock 76 or other mounting means at its proximal end. Stopcock 78 has a male luer lock 80 which attaches to female luer lock 76 of introducer 70. Male luer lock 80 and female luer lock 76 engage to form a gas tight seal to prevent gas from the insufflated abdominal cavity from escaping through the joint between stopcock 78 and introducer 70. An axial passageway 82 extends from the distal end of introducer 70 to its proximal end at luer lock 76. Stopcock 78 includes a valve assembly 84 having a valve handle 86 for opening and closing valve 84.

Figure 7A:
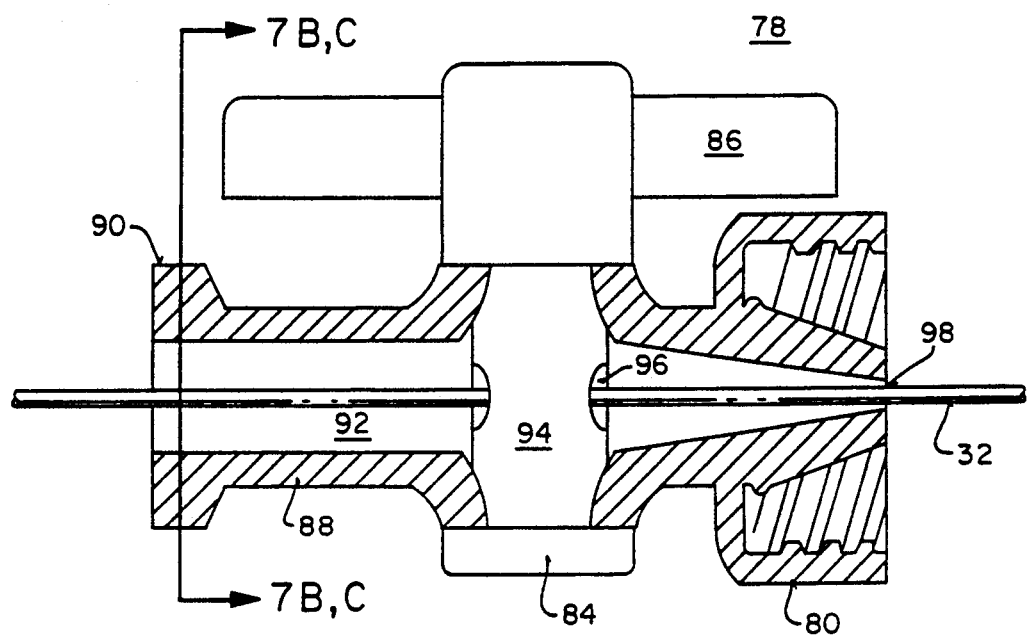
FIG. 7A is a front cross-sectional view of the stopcock of the FIG. 6.
Figures 7B, 7C:
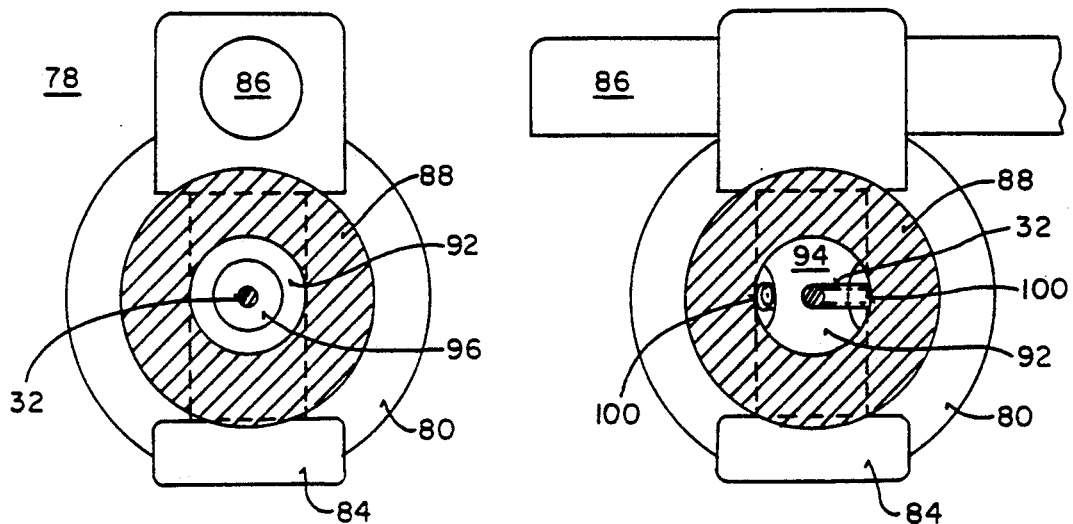
FIGS. 7B and 7C are top cross-sectional views of the stopcock of FIG. 7A.

Referring to FIGS. 7A-7C, stopcock 78 includes a body 88 with a male luer lock 80 at its distal end and female luer lock 90 at its proximal end, with an axial passageway 92 extending therebetween. Valve 84 extends through a middle portion of body 88 transversely, and includes a rotatable shaft 94 attached to valve handle 86. Shaft 94 has an orifice 96 which, when valve 84 is in an open position, is aligned with an axial passageway 92. When valve 84 is closed by rotating handle 86 90°, orifice 96 extends transversely to an axial passageway 92, and shaft 94 provides an air tight seal between distal end 98 and shaft 94.

The introducer/stopcock assembly provides retention of tether 32 extending from tethered clamp 24. As shown in FIG. 7A, tether 32 can be drawn through introducer 70 and through an axial passageway 92 and orifice 96 of stopcock 78. By tensioning tether 32, tethered clamp 24 and the tissue to which it is clamped may be positioned as desired, and this position maintained by rotating valve handle 86 on stopcock 78. When valve 84 is in an open position, as shown in FIG. 7B, tether 32 extends relatively straight through orifice 96 and an axial passageway 92. When handle 86 is rotated 90°, orifice 96 is rotated so as to extend transversely to an axial passageway 92, jamming portions of tether 32 against walls 100 of an axial passageway 92 and clamping tether 32 firmly in position.

Figure 8:
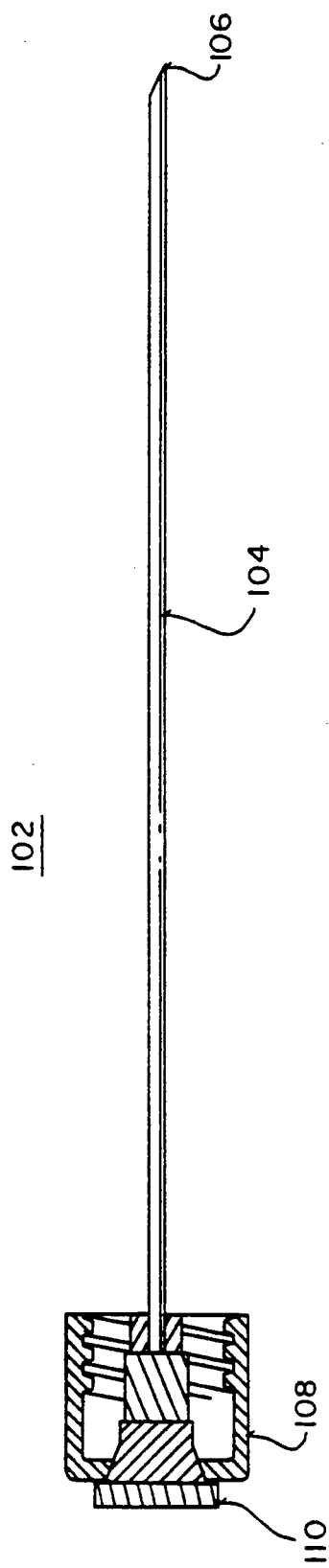
FIG. 8 is a front elevational view of an obturator constructed in accordance with the principles of the present invention.

In a further embodiment of the invention, an obturator 102 is provided for inserting introducer 70 into the abdomen. As shown in FIG. 8, obturator 102 includes a needle 104, usually comprising a 14 gauge needle of surgical steel. Needle 104 has a sharp point 106 for piercing the abdomen. At the proximal end of needle 104 is a hub 110 and interconnect 108, which usually comprises a male luer lock. Needle 104 may be inserted through an axial passageway 92 of stopcock 78 and an axial passageway 82 of introducer 70, with point 106 extending from the distal end 74 of introducer 70. Male luer lock 108 engages female luer lock 90 at the proximal end of stopcock body 88. Luer lock 108 prevents gas leakage through the proximal end of an axial passageway 92 of stopcock 78 when obturator 104 is positioned through introducer 70.

The invention further provides means for retrieving the tether 32 of tethered clamp 24. As shown in FIG. 9, a preferred embodiment of the means for retrieving the tether comprises a tethered snare 112 having an elongated rod 114, usually of stainless steel, with a hook 116 at its distal end. A male luer lock 118 is disposed at the proximal end of rod 114. When the introducer/stopcock assembly is in position in the abdomen, rod 114 of tether snare 112 can be inserted through an axial passageway 92 and orifice 96 of stopcock 78, and through an axial passageway 82 of introducer 70, such that hook 116 extends from the distal end of introducer 70. To prevent leakage of gas from the abdomen, male luer lock 118 engages with female luer lock 90 at the proximal end of stopcock 78. Tether snare 112 may then be positioned to retrieve tether 32 in hook 116 by tilting and rotating the introducer/stopcock assembly or longitudinally repositioning tether snare 112 within introducer 70. When tether 32 has been engaged by hook 116, male luer lock 118 may be released from luer lock 90 and tether snare 112 withdrawn from the introducer/stopcock assembly, drawing tether 32 through an axial passageway 82 of introducer 70, and an axial passageway 92 and orifice 96 of stopcock 78.

In an alternative embodiment, the tether snare is provided with a electrical connector 117 for connection to an electro-surgical radiofrequency generator. Connector 117 is coupled to rod 114. When RF current is supplied from the generator through the connector 117, hooked end 116 may be used to apply RF energy to the tissue at the desired site for advancing the introducer. In this way, in introducer 70 can be positioned in the abdominal cavity without using obturator 102 to pierce the tissue. In this embodiment, tether snare 112 is secured in the introducer/stopcock assembly, power cord 117 is connected to an electrosurgical generator, and the introducer/stopcock/tether snare assembly is percutaneously inserted by applying RF energy to the tissue.

Figure 11:
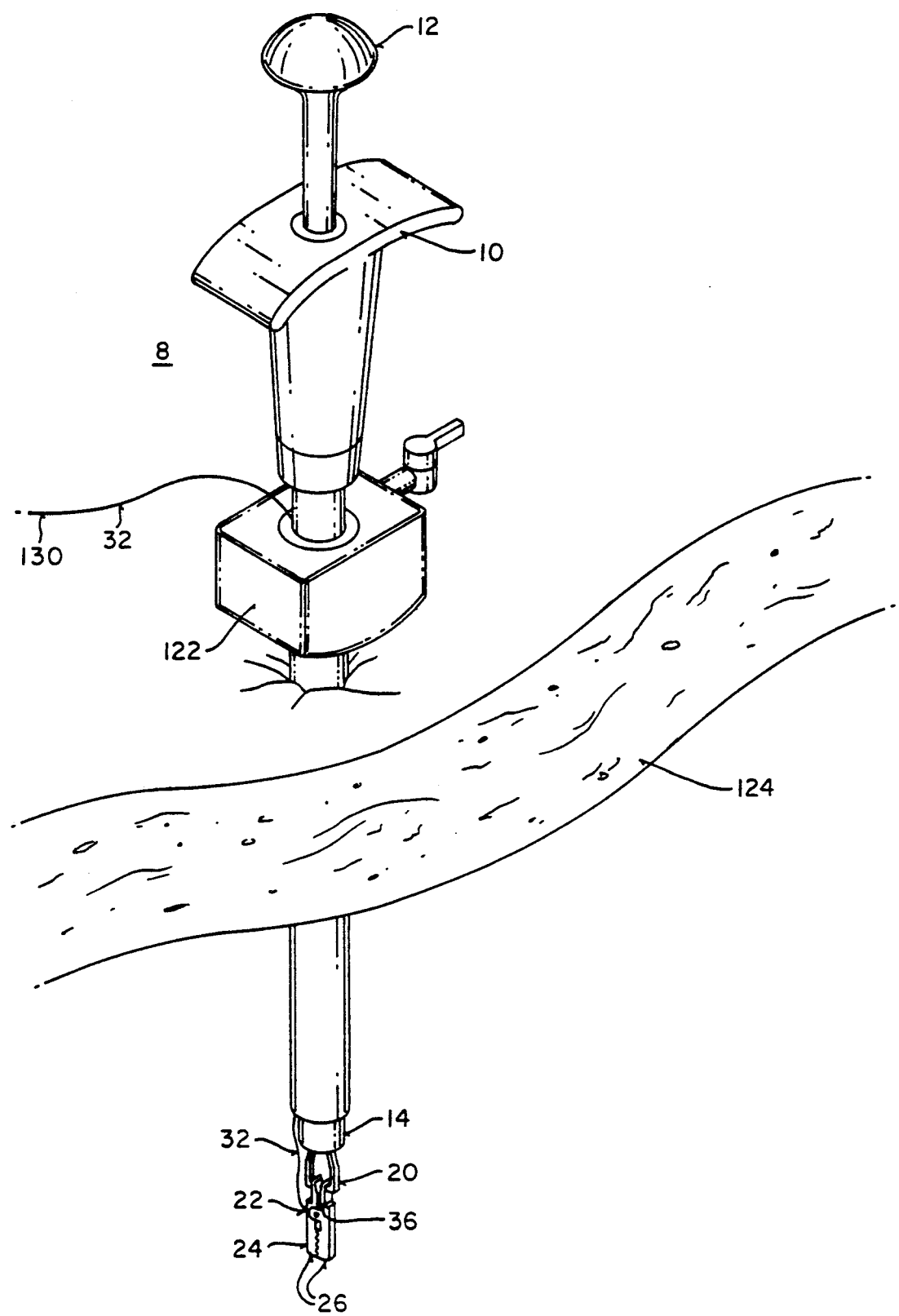
FIGS. 11-14 are perspective views of the clamp applicator of FIG. 1 positioned through a trocar sleeve in the abdominal wall in accordance with the principles of the present invention.

Referring now to FIGS. 11-17, a preferred embodiment of the method of the present invention will now be described. As shown in FIG. 11, a trocar sleeve 122 is inserted through the abdominal wall 124 using known techniques. The abdominal cavity will be distended using insufflation on other technique. Trocar sleeve 122 provides a sealed entryway into the abdominal cavity through which surgical instruments may be inserted. A clamp 24 is placed in arms 20 of the clamp applicator with tips 22 of arms 20 engaging lever arms 36 of clamp 24. Extension 14 of the clamp applicator with arms 20 and clamp 24 extending from the distal end is inserted through the trocar sleeve 122, with tether 32 extending through trocar sleeve 122 alongside extension 14 with the free end 130 of the tether outside of the abdominal cavity.

Figure 12:
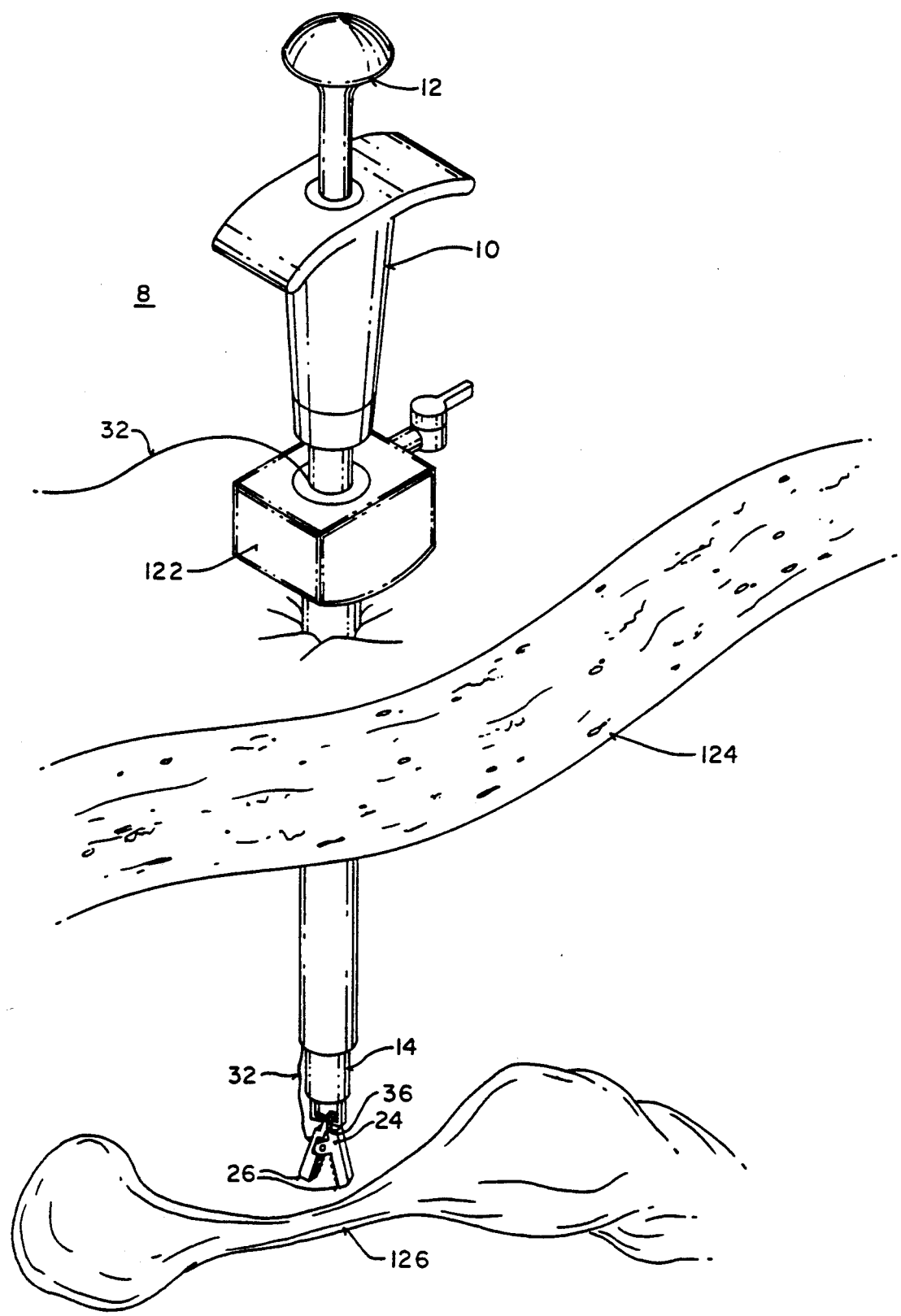

Referring now to FIG. 12, plunger 12 of the clamp applicator is pulled in a proximal direction away from handle 10, thereby retracting arms 20 and moving lever arms 36 together so as to open jaws 26 of clamp 24. The open clamp jaws 26 are then positioned over a tissue location 126 by longitudinal or angular movement of clamp applicator 8.

Figure 13:
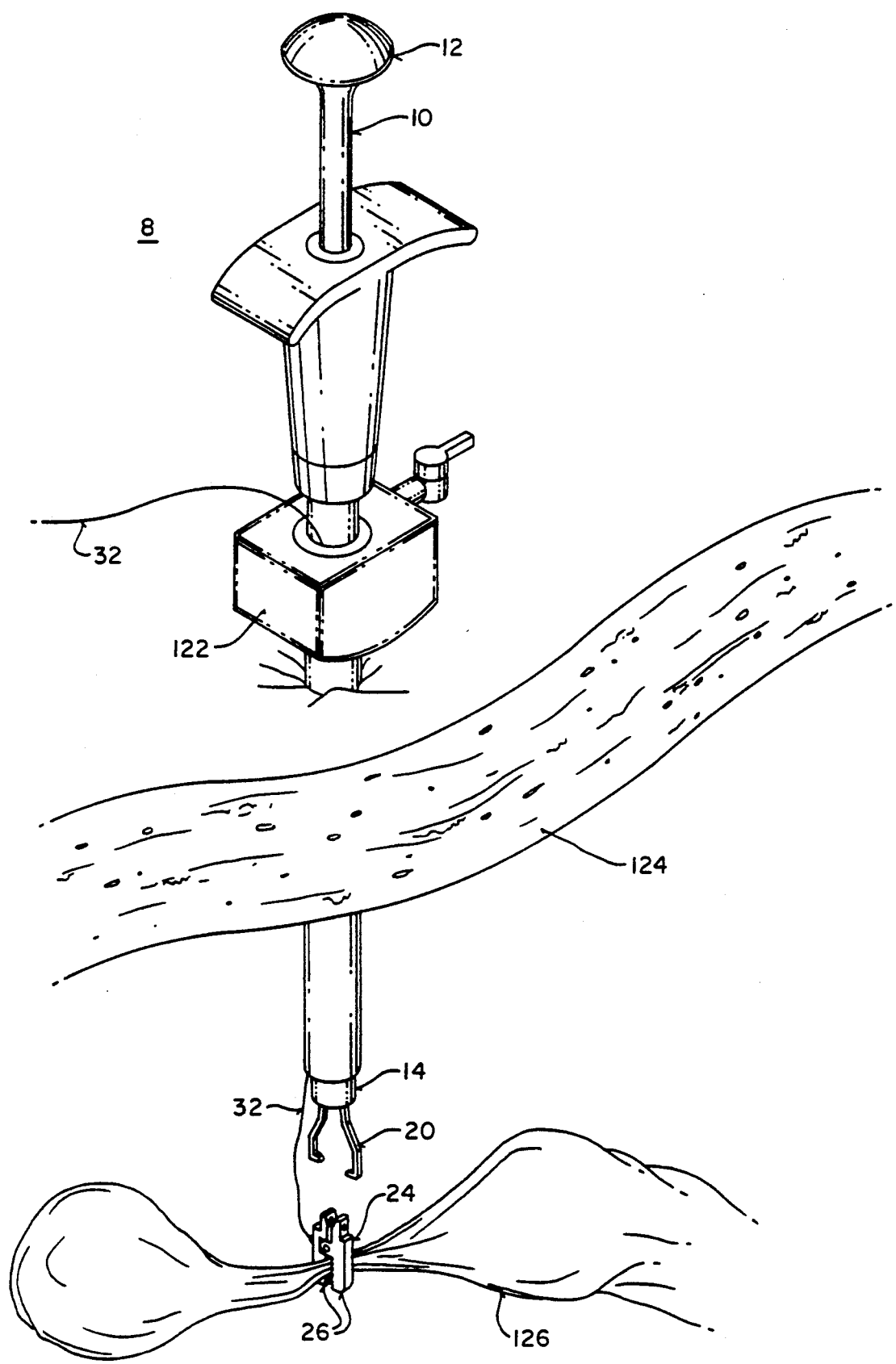

As shown in FIG. 13, when clamp 24 is positioned over tissue location 126, plunger 12 is pushed toward handle 10 fully extending arms 20 so as to close jaws 26 of clamp 24 and release clamp 24 from the clamp applicator.

Figure 14:
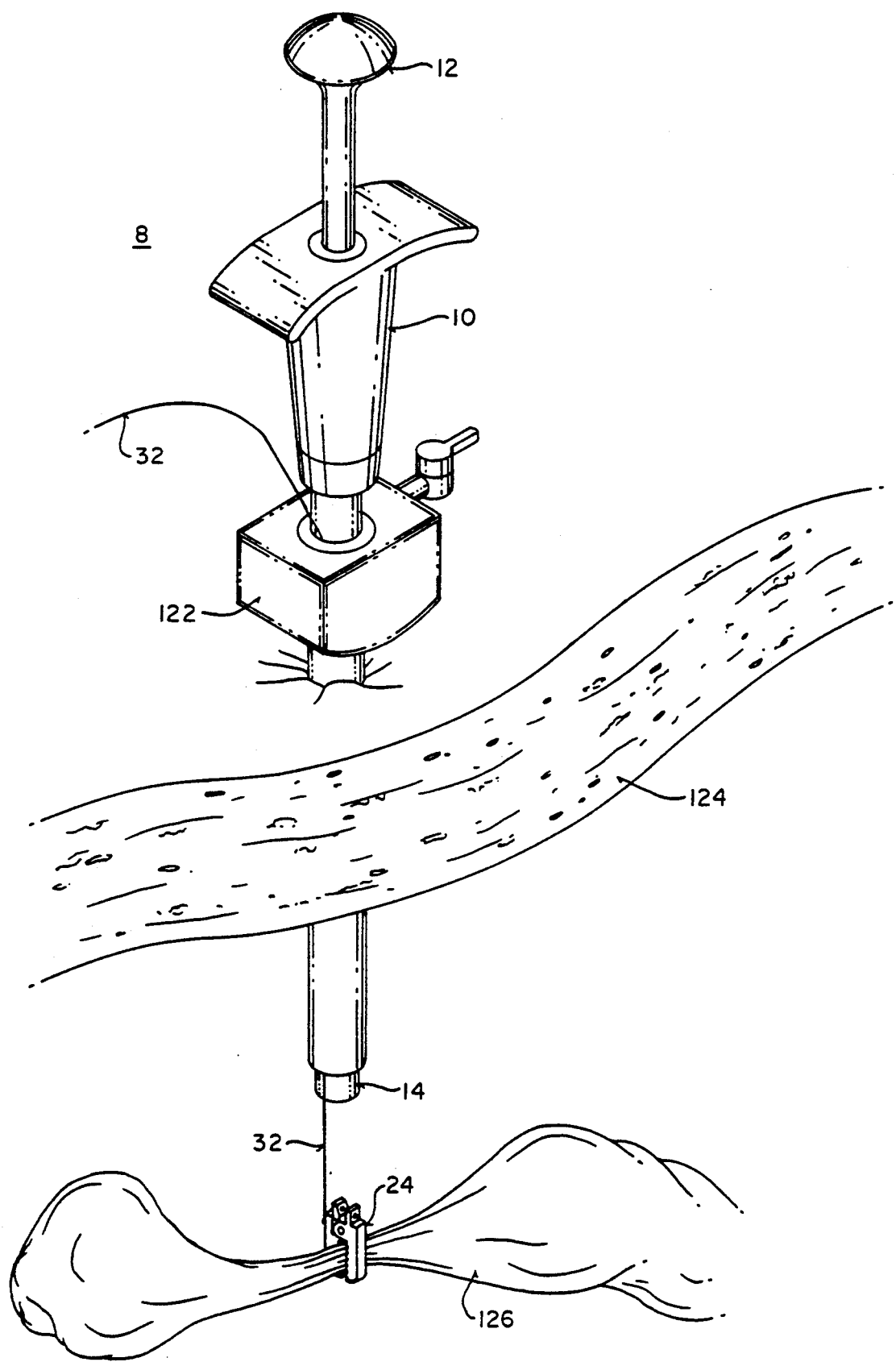

As seen in FIG. 14, clamp applicator 8 is then partially retracted from trocar sleeve 122 so as to tension tether 32 between trocar sleeve 122 and clamp 24. This facilitates retrieving tether 32 in subsequent steps described below.

Figure 15:
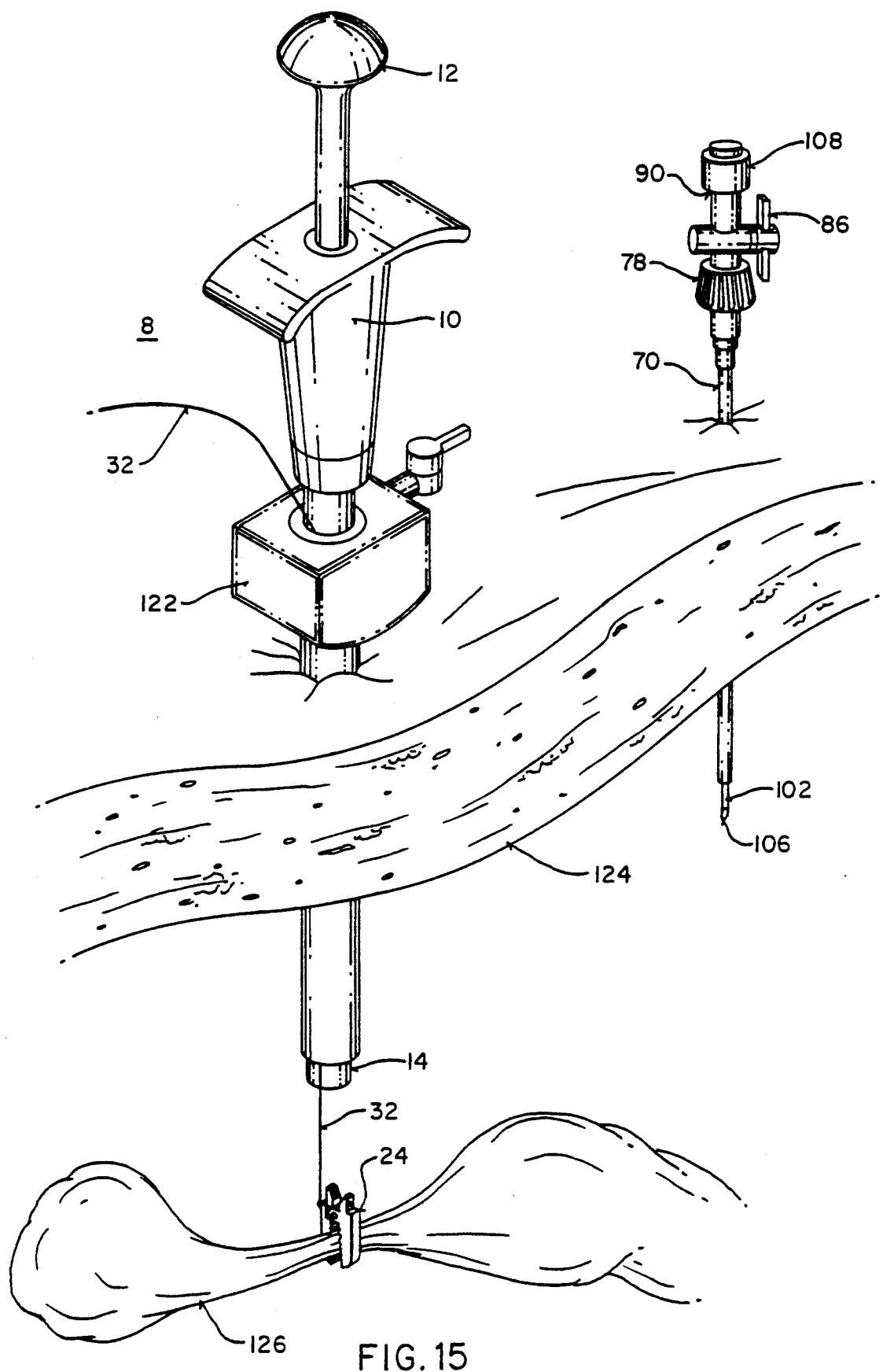
FIGS. 15-17 are perspective views of the clamp applicator of FIG. 1 positioned through a trocar sleeve in the abdominal wall with the introducer and stopcock of FIG. 6 positioned through the abdominal wall in accordance with the principles of the present invention.
Figure 16:
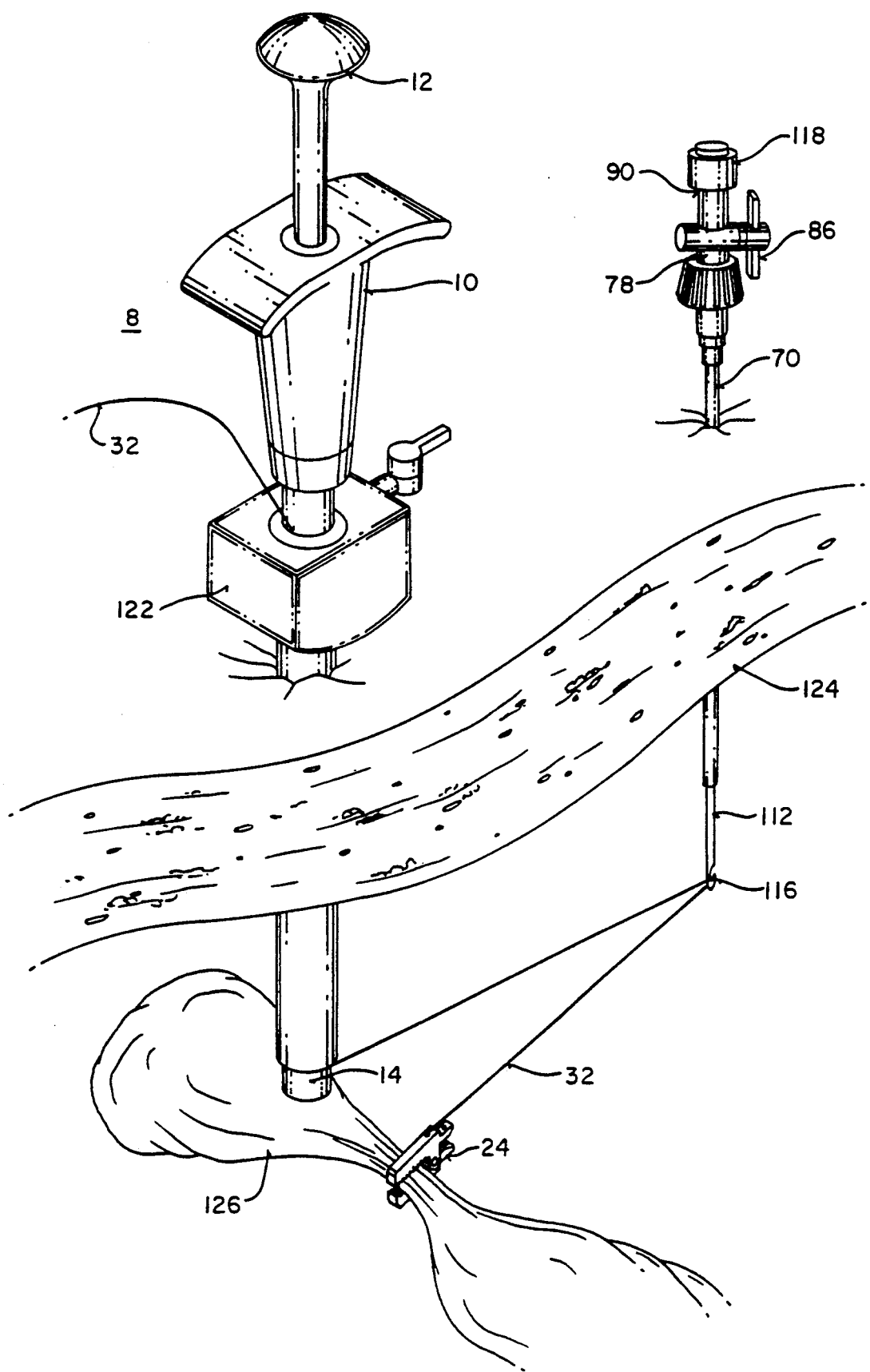

As illustrated in FIG. 15, introducer/stopcock assembly 70,78 is inserted through abdominal wall 124 using obturator 102 mounted in introducer 70. Obturator 102 is secured in introducer 70 by coupling male luer lock 108 to female luer lock 90 of stopcock 78. Point 106 facilitates piercing of abdominal wall 124 for insertion of introducer 70. When the introducer/stopcock assembly is in position, obturator 102 is withdrawn and gas leakage from the abdominal cavity is prevented by closing stopcock 78 using valve handle 86.

Alternatively, as described above, the introducer/stopcock assembly is inserted through the abdominal wall by placing the tether snare 112 in the introducer/stopcock 70, 78, connecting power cord 117 to an electro-surgical generator, and applying RF energy to the abdominal tissue at the desired location through hooked end 116.

To retrieve tether 32 of clamp 24, if the tether snare is not already in place in introducer 70, valve handle 86 is reopened and tether snare 112 is inserted through the introducer/stopcock assembly. Male luer lock 118 is secured to female luer lock 90 of stopcock 78. By moving the introducer/stopcock assembly 70, 78 and tether snare 112 longitudinally and angularly, hook 116 can be positioned to grasp tether 32 extending from clamp 24.

Figure 17:
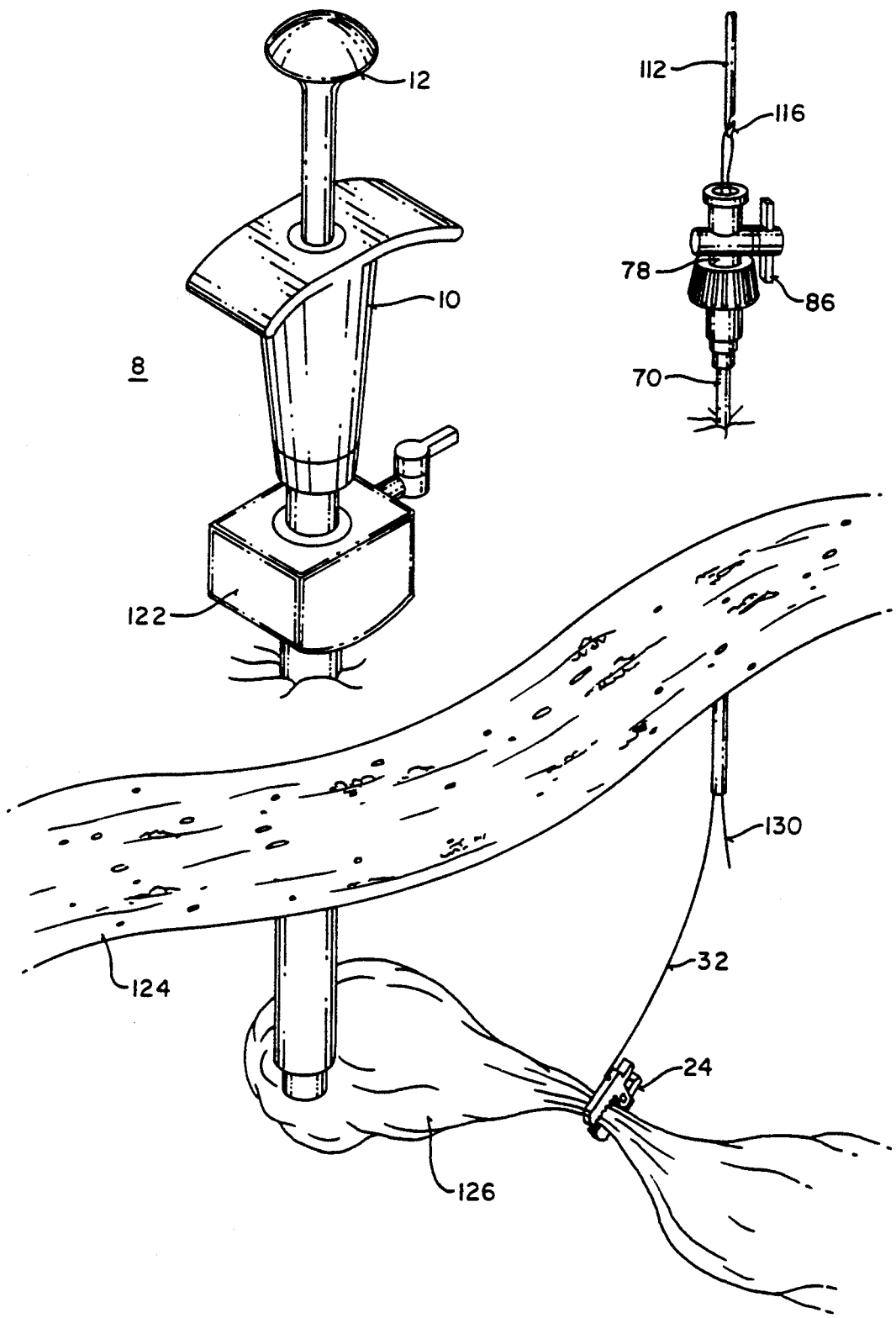

Referring now to FIG. 17, tether 32 is drawn through introducer 70 and stopcock 78 by withdrawing tether snare 112 back through the introducer/stopcock assembly. Tether 32 is drawn through the introducer/stopcock assembly until free end 130 has been pulled through the proximal end of stopcock 78. The portion of tether 32 now outside of the abdominal cavity can be tensioned so as to position tissue location 126 as desired. When a desired position has been achieved, tether 32 can be locked in place by rotating valve handle 86 of stopcock 78. The subsequent steps of the surgical procedure may then be performed with tissue location 126 maintained in a stationary position.

In an alternative embodiment, the tether has a second clamp, hook, or other tissue engaging means detachably coupled to its free end. In this embodiment, the tether is tensioned to position the clamp 24 and the tissue engaging means at the free end is attached to a second portion of tissue, usually within the abdominal cavity, to maintain clamp 24 in position.

When the tissue positioning is no longer required, tension on tether 32 is relieved by rotating valve handle 86 (or releasing the tissue engaging means at the free end of the tether). Clamp applicator 8 is reinserted through trocar sleeve 122 and plunger 12 depressed toward handle 10 of the applicator to extend arms 20.

Arms 20 are then positioned over lever arms 36 of clamp 24, and plunger 12 is pulled in a proximal direction to close arms 20 on lever arms 36, thereby opening jaws 26 of the clamp. Clamp applicator 8 is then withdrawn from trocar sleeve 122, pulling with it clamp 24 and tether 32. Valve handle 86 may then be rotated to close stopcock 78, preventing gas leakage through introducer 70.

While the above is a complete description of the preferred embodiments of the invention, various alternatives, modifications and equivalents may be used. Therefore, the above description should not be taken as limiting the scope of the invention which is defined by the appended claims.

What is claimed is:

1. A tissue manipulation system comprising:
   a clamp having a pair of movable jaws, a pair of levers connected to the jaws for closing and opening the jaws and a hinge disposed between the levers and the jaws;
   means for applying the clamp through a percutaneous cannula to a first tissue site, said means for applying having a tubular portion for sealing within the cannula; and
   a flexible tether having a first end attached to the clamp and a free end opposite the first end for remotely manipulating the clamp.

2. A tissue manipulation system as in claim 1 wherein the means for applying the clamp comprises:
   an elongated tubular body with a distal end, a proximal end and an axial passageway therebetween;
   a pair of movable arms disposed at the distal end, each arm configured to engage one of the levers of the clamp;
   means at the proximal end of the body for actuating the arms; and
   a linkage disposed in the axial passageway, the linkage connecting the arms to the means for actuating.

3. A tissue manipulation system as in claim 1 further comprising means sealable within a percutaneous cannula for retrieving the free end of the tether.

4. A tissue manipulation system as in claim 3 wherein the means for retrieving the tether comprises an elongated snare having a hooked distal end for grasping the tether and means at a proximal end for sealing the percutaneous cannula.

5. A tissue manipulation system as in claim 1 further comprising means separated from the clamp for retaining the tether.

6. A tissue manipulation system as in claim 5 wherein the means for retaining comprises a introducer comprising a shaft having a distal end, a proximal end and an axial passage therebetween, and a retainer disposed at the proximal end of the introducer, wherein the distal end is percutaneously positionable to allow the tether to be passed through the axial passageway and detachably secured in the retainer.

7. A tissue manipulation system as in claim 6 wherein the retainer comprises a stopcock having a housing with a bore therethrough and a valve for closing off the bore, whereby the tether may be positioned in the bore and engaged by the valve.

8. A tissue manipulation system as in claim 5 wherein the means for retaining the tether comprises means attached to the tether and separated from the first clamp for engaging a second tissue site.

9. A tissue manipulation system as in claim 1 wherein the clamp further comprises means for biasing the jaws in a closed configuration.

10. A tissue manipulation system as in claim 2 wherein the clamp applying means includes means for biasing the arms in an open configuration.

11. A tissue manipulation system as in claim 2, wherein the means for actuating the arms comprises a tubular handle and a plunger slidably mounted in the handle, the plunger being coupled to the linkage.

12. A tissue manipulation system comprising:
    a clamp having a pair of movable jaws, a pair of levers connected to the jaws for opening and closing the jaws and a hinge disposed between the levers and the jaws;
    a flexible tether having a first end attached to the clamp and a free end opposite the first end for remotely manipulating the clamp; and
    a introducer comprising a shaft having a proximal end, a distal end, an axial passage therebetween and means at the proximal end for sealing the axial passage, wherein the distal end is percutaneously positionable to allow the free end of the tether to be drawn through the axial passage.

13. A tissue manipulation system as in claim 12 further comprising means for holding a portion of the tether in tension.

14. A tissue manipulation system as in claim 13 wherein the means for holding comprises a stopcock disposed at the proximal end of the introducer.

15. A tissue manipulation system as in claim 12 further comprising means sealable within the introducer for retrieving the free end of the tether and drawing the free end through the axial passage of the introducer.

16. A tissue manipulation system as in claim 14 wherein the means for retrieving and drawing comprises an elongated snare having a hooked distal end configured to pass through the axial passage of the introducer and means at a proximal end for sealing the axial passage.

17. A tissue manipulation system as in claim 12 further comprising means for percutaneously inserting the introducer.

18. A tissue manipulation system as in claim 17 wherein the means for inserting the introducer comprises an obturator removably disposed in the axial passage of the introducer.

19. A tissue manipulation system as in claim 12 further comprising means for percutaneously applying the clamp to the tissue through a percutaneous cannula.

20. A tissue manipulation system as in claim 19 wherein the means for applying comprises:
    an elongated tubular body having a distal end, a proximal end and an axial passageway therebetween;
    a pair of movable arms disposed at the distal end of the body, each arm configured to engage one of the levers of the clamp;
    means at the proximal end of the body for actuating the arms; and
    a linkage disposed in the axial passageway and connecting the arms to the means for actuating.

21. A tissue manipulation system comprising:
    a clamp having a pair of movable jaws, a pair of levers connected to the jaws for opening and closing the jaws and a hinge disposed between the levers and the jaws;
    a flexible tether having a first end coupled to the clamp and a free end opposite the first end;

means for percutaneously applying the clamp to tissue through a percutaneous cannula;

a introducer comprising a shaft having a proximal end, a distal end, an axial passage therebetween and means at the proximal end for sealing the axial passage, the distal end being percutaneously positionable, whereby the tether may be passed through the axial passage; and means on the proximal end of the introducer for retaining the tether which passes through the axial passage.

22. A tissue manipulation system as in claim 21 wherein the means for applying comprises:

an elongated tubular body having a distal end, a proximal end and an axial passageway therebetween;

a pair of movable arms disposed at the distal end of the body, each arm configured to engage one of the levers of the clamp;

means at the proximal end of the body for actuating the arms; and a linkage disposed in the axial passageway and connecting the arms to the means for actuating.

23. A tissue manipulation system as in claim 21 further comprising means sealable within the introducer for retrieving the free end of the tether and drawing the free end through the axial passage of the introducer.

24. A tissue manipulation system as in claim 23 wherein the means for retrieving the free end comprises an elongated snare with a hooked distal end configured to pass through the axial passage of the introducer and means at a proximal end for sealing the axial passage.

25. A tissue manipulation system as in claim 24 further comprising means for percutaneously inserting the introducer into a patient.

26. A tissue manipulation system as in claim 25 wherein the means for inserting the introducer comprises an obturator having a distal point for piercing tissue.

27. A tissue manipulation system as in claim 25 wherein the means for inserting the introducer comprises means disposed at the distal end of the introducer for applying radiofrequency current to tissue.

28. A tissue manipulation system as in claim 25 wherein the hooked end of the tether snare is conductive, the tether snare further comprising means at the proximal end of the snare for connecting to a radiofrequency generator and a conductive rod extending between the means for connecting and the hooked end, whereby the radiofrequency energy may be applied to the tissue using the hooked end.

29. A tissue manipulation system as in claim 21 wherein the clamp further comprises means for biasing the jaws in a closed configuration.

30. A tissue manipulation system as in claim 22 wherein the means for applying a clamp further comprises means for biasing the arms in an open configuration.

31. A method for manipulating tissue comprising the steps of:

introducing a clamp through a percutaneous cannula to a tissue location using an applicator which seals within the cannula;

securing the clamp to the tissue location; and tensioning a free end of a tether attached to the clamp to manipulate the tissue.

32. The method of claim 31 wherein the step of tensioning comprises pulling the tether through a percutaneous introducer.

33. The method of claim 32 further comprising the step of securing the tether relative to the introducer after the tensioning step.

34. The method of claim 33 wherein the step of securing the tether comprises actuating a retainer disposed at a proximal end of the introducer.

35. The method of claim 33 wherein the step of securing the tether comprises securing to a second tissue location means attached to the tether for engaging tissue.

36. The method of claim 32 wherein the percutaneous introducer is positioned using an obturator removably mounted in the introducer.

37. The method of claim 32 wherein the tether is pulled through the percutaneous introducer by inserting a tether snare having a hooked end through the introducer, engaging the tether with the hooked end, and retracting the tether snare with the tether in the hooked end from the introducer.

38. The method of claim 37 wherein the introducer is positioned by applying radiofrequency energy to tissue where the introducer is to be positioned.

39. The method of claim 38 wherein the radiofrequency energy is applied through the hooked end of the tether snare with the tether snare positioned in the introducer.

* * * * *